(12) United States Patent
Yoshii et al.

(10) Patent No.: US 9,107,404 B2
(45) Date of Patent: Aug. 18, 2015

(54) METHOD FOR REDUCING UNDESIRABLE EFFECTS ON TURFGRASS

(75) Inventors: Hiroshi Yoshii, Kusatsu (JP); Tomoaki Kezuka, Osaka (JP); Ryu Yamada, Kusatsu (JP); Ema Mitsuno, Osaka (JP); Takashi Terada, Kusatsu (JP)

(73) Assignee: Ishihara Sangyo Kaisha, Ltd., Osaka-shi (JP)

( * ) Notice: Subject to any disclaimer, the term of this patent is extended or adjusted under 35 U.S.C. 154(b) by 0 days.

(21) Appl. No.: 13/582,321

(22) PCT Filed: Mar. 2, 2011

(86) PCT No.: PCT/JP2011/054800
§ 371 (c)(1),
(2), (4) Date: Aug. 31, 2012

(87) PCT Pub. No.: WO2011/108607
PCT Pub. Date: Sep. 9, 2011

(65) Prior Publication Data
US 2012/0322656 A1 Dec. 20, 2012

(30) Foreign Application Priority Data
Mar. 3, 2010 (JP) ................................. 2010-046200

(51) Int. Cl.
*A01N 25/30* (2006.01)
*A01N 25/32* (2006.01)
*A01P 13/00* (2006.01)

(52) U.S. Cl.
CPC ................ *A01N 25/30* (2013.01); *A01N 25/32* (2013.01)

(58) Field of Classification Search
None
See application file for complete search history.

(56) References Cited

U.S. PATENT DOCUMENTS

| 4,744,814 | A | 5/1988 | Kimura et al. | |
|---|---|---|---|---|
| 6,573,217 | B2 * | 6/2003 | Bickers et al. | 504/212 |
| 2003/0104944 | A1 | 6/2003 | Humble et al. | |
| 2007/0238616 | A1 | 10/2007 | Parrish | |

FOREIGN PATENT DOCUMENTS

| CN | 1052409 A | 6/1991 |
|---|---|---|
| CN | 1241904 A | 1/2000 |
| CN | 1444448 A | 9/2003 |
| CN | 101228879 A | 7/2008 |
| JP | 47 50380 | 12/1972 |
| JP | 02-073002 | 3/1990 |
| JP | 2 504644 | 12/1990 |
| JP | 5 25010 | 2/1993 |
| JP | 8 333204 | 12/1996 |
| JP | 2004 504331 | 2/2004 |
| WO | WO 2006/030917 A1 | 3/2006 |
| WO | WO 2007/042447 A2 | 4/2007 |

OTHER PUBLICATIONS

Willis et al., "Distance and Severity of Creeping Bentgrass Injury from Mower-Dislodged Sulfonylurea Herbicides", 2008, Weed Technology, vol. 22, pp. 263-266.*
Helena Chemical Company, Kinetic Product Label, 2002, pp. 1-2.*
International Search Report Issued May 10, 2011 in PCT/JP11/54800 Filed Mar. 2, 2011.
Chinese Office Action issued May 30, 2013, in China Patent Application No. 201180011954.7 (with English translation).
Yu Zhang, et al., "The Characteristics and Uses of Silicone Surfactant as Pesticide Additive", Materials Research and Application, vol. 2, No. 4, Dec. 2008, pp. 424-426.
Office Action in corresponding Japanese application No. 2011-043816, dated Aug. 19, 2014. (w/English Translation).

* cited by examiner

*Primary Examiner* — Michael B Pallay
(74) *Attorney, Agent, or Firm* — Oblon, McClelland, Maier & Neustadt, L.L.P.

(57) ABSTRACT

To provide a method for managing a lawn at a site, such as a golf course, where turfgrass less sensitive to herbicides and turfgrass highly sensitive to herbicides are used in combination, without causing undesirable effects on the highly sensitive turfgrass. A herbicidal compound and a silicone surfactant are applied to a site where turfgrass less sensitive to the herbicidal compound is planted, thereby to reduce undesirable effects on nearby turfgrass highly sensitive to the herbicidal compound.

12 Claims, No Drawings

METHOD FOR REDUCING UNDESIRABLE EFFECTS ON TURFGRASS

TECHNICAL FIELD

The present invention relates to a method for reducing undesirable effects on turfgrass highly sensitive to herbicidal compounds.

BACKGROUND ART

Heretofore, various herbicidal compounds are used for the lawns. For example, in management of a lawn at a golf course, it has become indispensable to use a herbicidal compound. At a golf course, plural types of turfgrasses are planted in many cases, and it is often a case where turfgrass less sensitive to a herbicidal compound to be used and turfgrass highly sensitive thereto are used in combination. In such a case, a certain restriction is required in the use of the herbicidal compound, and the situation has not been necessarily satisfactory from the viewpoint of the operation efficiency, costs, etc.

Flazasulfuron is known as a herbicidal compound (Patent Document 1). Warm-season turfgrass such as mascarenegrass or Japanese lawngrass is less sensitive to flazasulfuron and thus is safe thereto. Further, flazasulfuron can control unwanted plants and thus is an excellent compound. On the other hand, cool-season turfgrass such as bentgrass, bluegrass or ryegrass is relatively highly sensitive to flazasulfuron, and flazasulfuron may sometimes present undesirable effects thereto.

As mentioned above, in a golf course, plural types of turfgrasses are planted in many cases. For example, warm-season turfgrass which is safe to flazasulfuron may be planted in fairways, etc., and cool-season turfgrass which is highly sensitive to flazasulfuron, may be planted in putting greens, etc. Flazasulfuron is usually applied to a site where warm-season turfgrass is planted, but immediately after the application or even after expiration of a certain period after the application, in a situation where morning dew or the like is observed, flazasulfuron is likely to attach to soles of shoes of players walking on the warm-season turfgrass, and if the players walk on the green in such a state, undesirable effects may be brought about against the cool-season turfgrass planted in the green. Further, other than via soles of shoes of players, etc., for example, via a chemical treatment tool to apply various chemicals, a watering tool to sprinkle water to turfgrass, etc., or a lawn-mowing tool such as a lawn mower, undesirable effects may be brought about on the cool-season turfgrass.

Such a problem is not limited to with respect to flazasulfuron and may be present with respect to any herbicidal compound, to which the sensitivity is different depending upon the types of turfgrasses.

PRIOR ART DOCUMENT

Patent Document

Patent Document 1: U.S. Pat. No. 4,744,814

DISCLOSURE OF INVENTION

Technical Problem

It is an object of the present invention to provide a method for managing a lawn at a site, such as a golf course, where turfgrass less sensitive to a herbicidal compound to be used and turfgrass highly sensitive thereto are used in combination, without causing undesirable effects on the highly sensitive turfgrass.

Solution to Problem

As a result of a study to solve the above problem, it has been unexpectedly found to solve the above problem by using a silicone surfactant.

That is, the present invention relates to a method wherein a herbicidal compound and a silicone surfactant are applied, by such a means as spraying, to a site where turfgrass less sensitive to the herbicidal compound is planted, thereby to reduce undesirable effects on nearby turfgrass highly sensitive to the herbicidal compound. Such undesirable effects may, for example, be discoloring, brown discoloration, necrosis, chlorosis, anthocyan, growth inhibition, etc.

The present invention provides the following.

(1) A method for reducing undesirable effects on turfgrass, which comprises applying a herbicidal compound and a silicone surfactant to a site where turfgrass less sensitive to the herbicide compound is planted, thereby to reduce undesirable effects on nearby turfgrass highly sensitive to the herbicidal compound.

(2) The method according to the above (1), wherein the herbicidal compound is at least one member selected from the group consisting of acetolactate synthase (ALS) inhibitors and mitotic inhibitors.

(3) The method according to the above (2), wherein the herbicidal compound is an acetolactate synthase (ALS) inhibitor.

(4) The method according to the above (3), wherein the acetolactate synthase (ALS) inhibitor is at least one compound or its salt selected from the group consisting of a sulfonylurea compound, a pyrimidine compound and a triazolopyrimidine compound.

(5) The method according to the above (4), wherein the sulfonylurea compound is at least one compound selected from the group consisting of flazasulfuron, cinosulfuron, rimsulfuron, trifloxysulfuron, chlorimuron ethyl, iodosulfuron methyl, foramsulfuron, nicosulfuron, sulfosulfuron and chlorosulfuron, the pyrimidine compound is pyrimisulfan, and the triazolopyrimidine compound is florasulam.

(6) The method according to the above (4), wherein the sulfonylurea compound is at least one compound selected from the group consisting of flazasulfuron, rimsulfuron, trifloxysulfuron and nicosulfuron, and the triazolopyrimidine compound is florasulam.

(7) The method according to the above (2), wherein the herbicidal compound is a mitotic inhibitor.

(8) The method according to the above (7), wherein the mitotic inhibitor is a carbamate compound.

(9) The method according to the above (8), wherein the carbamate compound is asulam.

(10) The method according to the above (1), wherein the silicone surfactant is an organically modified silicone surfactant.

(11) The method according to the above (10), wherein the organically modified silicone surfactant is a polyether modified silicone surfactant.

(12) The method according to the above (11), wherein the polyether modified silicone surfactant is a compound represented by the following formula (I):

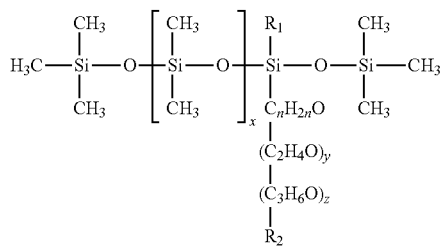

wherein $R_1$ is a hydrogen atom or a methyl group, $R_2$ is a hydrogen atom, a hydroxy group, a methyl group or an acetyl group, n is an integer of from 0 to 4, x is an integer of from 0 to 2, y is an integer of from 1 to 15, and z is an integer of from 0 to 10.

(13) The method according to the above (1), wherein the herbicidal compound is diluted with water containing the silicone surfactant in a proportion of from 0.005 to 0.5 vol % and applied to the site where turfgrass less sensitive to the herbicide compound is planted.

(14) The method according to any one of the above (1) to (13), wherein the undesirable effects are caused via contact with turfgrass or unwanted plants at the site to which the herbicidal compound and the silicone surfactant are applied.

(15) The method according to any one of the above (1) to (13), wherein the undesirable effects are caused via a shoe sole, a chemical treatment tool, a watering tool or a lawn-mowing tool contacted with turfgrass or unwanted plants at the site to which the herbicidal compound and the silicone surfactant are applied.

Advantageous Effects of Invention

According to the present invention, it is possible to provide a method for managing a lawn, whereby the operation efficiency, costs, etc. may be improved.

DESCRIPTION OF EMBODIMENTS

A surfactant is used in combination with a herbicidal compound usually for the purpose of increasing the effects. When a herbicidal compound and a surfactant are used at a site where turfgrass less sensitive to the herbicidal compound to be used and turfgrass highly sensitive thereto are planted in the vicinity to each other, undesirable effects to the highly sensitive turfgrass may sometimes be brought about, but by using a silicone surfactant among various surfactants, it is possible to reduce such undesirable effects.

The silicone surfactant serves to lower the surface tension to plants, of the treating liquid containing a herbicidal compound and to impart a proper spreading property. Although the reason is not clearly understood, it is considered that by such effects of the silicone surfactant, transfer of the herbicidal compound from the plants at the treated site is prevented, which contributes to development of the effects of the present invention.

The silicone surfactant of the present invention is preferably an organically modified silicone surfactant. In the present invention, "an organically modified silicone surfactant" is meant mainly for a silicone oil having hydrophilicity imparted by introduction of an organic group such as a polyether substituent. In such an organically modified silicone surfactant, as the organic group to be introduced, various ones are known in addition to the above polyether substituent, and they may also be used so long as they are suitable for the purpose of the present invention. As the organically modified silicone surfactant, a polyether modified silicone surfactant is preferred.

An example of the organically modified silicone surfactant having a polyether substituent introduced (i.e. the polyether modified silicone surfactant) may preferably be polyoxyethylene methyl-polysiloxane, polyoxyalkylene methyl-polysiloxane, ethoxylated trisiloxane, polyether polymethyl-siloxane copolymer, polyether polymethyl-siloxane copolymer, or a compound represented by the following formula (I):

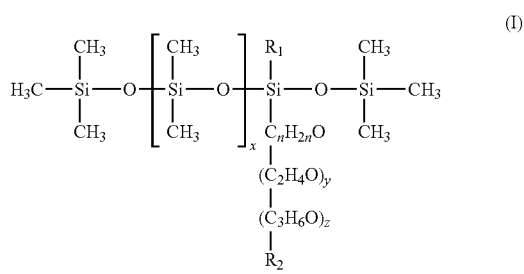

wherein $R_1$ is a hydrogen atom or a methyl group, $R_2$ is a hydrogen atom, a hydroxy group, a methyl group or an acetyl group, n is an integer of from 0 to 4, x is an integer of from 0 to 2, y is an integer of from 1 to 15, and z is an integer of from 0 to 10. However, the present invention is by no means limited thereto.

Here, in a case where the silicone surfactant is a compound represented by the above formula (I), a compound wherein x is 0 is preferred from the viewpoint of the spreading property.

As specific examples of the silicone surfactant, the following ones (tradenames) may, for example, be preferred. Further, among commercially available silicone surfactants, there are ones which further contain other components.

Maku-pika (polyoxyethylene methyl-polysiloxane manufactured by Ishihara Sangyo Kaisha, Ltd.)

KF-640 (polyoxyalkylene methyl-polysiloxane, manufactured by Shin-Etsu Chemical Co., Ltd.)

Silwet L-77, Silwet 408, Silwet ECO (ethoxylated trisiloxane, manufactured by Momentive performance materials, Witco, etc.)

Break-Thru (polyether polymethyl-siloxane copolymer, manufactured by Evonik Goldschmidt Chemical Corporation)

Breakthru (polyether polymethyl-siloxane copolymer, manufactured by Sankei Chemical Co., Ltd.)

The herbicidal compound may be a compound, to which the sensitivity is different depending upon the types of turfgrasses. In a case where turfgrass less sensitive to such a compound and turfgrass highly sensitive thereto are planted in the vicinity of each other, even if such a compound is applied to a site where the less sensitive turfgrass is planted, undesirable effects may sometimes be brought about against the highly sensitive turfgrass via direct or indirect contact with mainly plants (such as turfgrass, unwanted plants, etc.) at the treated site.

For example, in a golf course, turfgrass less sensitive to a herbicidal compound and turfgrass highly sensitive thereto may be planted in the vicinity of each other, e.g. in fairways and greens, etc. Even if the herbicidal compound is applied to a site where the less sensitive turfgrass is planted, such a herbicidal compound may be brought in contact with the highly sensitive turfgrass via direct or indirect contact. In such a case, undesirable effects may be brought about against the highly sensitive turfgrass, even though the herbicidal compound is not applied directly to the highly sensitive turfgrass.

In the present invention "direct or indirect contact" means that when the herbicidal compound is applied to a site where the less sensitive turfgrass is planted, it is brought in contact via e.g. soles of shoes of golf players or workers, which were in contact with e.g. turfgrass or unwanted plants, etc. at the treated site; a chemical treatment tool to apply various agricultural chemicals (e.g. hoses or wheels of a chemical treatment tool); a watering tool for sprinkling water to turfgrass, etc. (e.g. hoses or wheels of a watering tool); a lawn-mowing tool (e.g. a lawn mower or its wheels); etc.

In the present invention, "planted in the vicinity of each other" means that the turfgrasses are planted in such a state that the above mentioned direct or indirect contact may occur. For example, a case may be mentioned where the less sensitive turfgrass and the highly sensitive turfgrass are planted adjacent to each other or with a distance from each other. Further, in a golf course, a plurality of holes are provided in the same premises, and not only within the same hole, but also among different holes, the direct or indirect contact may occur. In the present invention, such a situation is also included in the expression "planted in the vicinity of each other".

The present invention is to solve such a problem associated with the herbicidal compound having such a nature and background, and the chemical structure, amount, etc. of the applicable herbicidal compound are not particularly limited.

As an example of the herbicidal compound applicable to the present invention, preferred is, for example, an acetolactate synthase (ALS) inhibitor or a mitotic inhibitor. The acetolactate synthase (ALS) inhibitor may, for example, be preferably a sulfonylurea compound such as flazasulfuron, cinosulfuron, rimsulfuron, trifloxysulfuron, chlorimuron ethyl, iodosulfuron methyl, foramsulfuron, nicosulfuron, sulfosulfuron or chlorosulfuron; a pyrimidine compound such as pyrimisulfan; a triazolopyrimidine compound such as florasulam; or their salts. The mitotic inhibitor may, for example, be preferably a carbamate compound such as asulam, or its salts. Among them, flazasulfuron, rimsulfuron, trifloxysulfuron, nicosulfuron, florasulam, asulam or their salts are, for example, preferred. The salt is preferably an alkaline earth metal salt or an alkali metal salt, and a sodium salt is particularly preferred.

Further, the turfgrass less sensitive to the herbicidal composition or the turfgrass highly sensitive thereto, is known in this field.

For example, as the turfgrass less sensitive to flazasulfuron, rimsulfuron, trifloxysulfuron or nicosulfuron, warm-season turfgrass such as mascarenegrass or Japanese lawngrass may, for example, be mentioned, and as the turfgrass highly sensitive to such a compound, cool-season turfgrass such as bentgrass, bluegrass or ryegrass may, for example, be mentioned.

The amount of the silicone surfactant to be used cannot be generally be defined, since it is required to be suitably adjusted depending upon the weather conditions, the types and sizes of weeds to be controlled, the state of turfgrasses to be treated, etc. However, with a view to imparting a proper surface tension and spreading property at the time when a formulated herbicidal compound is diluted with water and applied, thereby to effectively obtain the effects of the present invention, it is preferred to mix the surfactant to such water in a proportion of from 0.005 to 0.5 vol %, more preferably in a proportion of from 0.01 to 0.25 vol %.

With a view to effectively obtaining the effects of the present invention, the amount of the treating liquid containing the herbicidal compound and the silicone surfactant is preferably from 100 to 5,000 L (liters), more preferably from 150 to 4,000 L, per one hectare. However, the amount of the silicone surfactant and the amount of the treating liquid may suitably be selected to be outside such ranges, depending upon various conditions such as the above mentioned weather conditions, etc.

In the case of an ALS inhibitor, the amount of the herbicidal compound is preferably from 1 to 200 g, more preferably from 10 to 150 g, per one hectare of turfgrass. In the case of a mitotic inhibitor, the amount is preferably from 500 to 6,000 g, more preferably from 1,000 to 5,000 g, per one hectare of turfgrass.

Further, the concentration of the herbicidal compound in the treating liquid containing the herbicidal compound and the silicone surfactant, to be sprayed or applied to the turfgrass, is preferably from 0.00002 to 0.2 mass %, more preferably from 0.00025 to 0.1 mass %, in the case of an ALS inhibitor. In the case of a mitotic inhibitor, such a concentration is preferably from 0.01 to 6 mass %, more preferably from 0.025 to 3.5 mass %.

Although the reason as to why the effects of the present invention are obtainable, is not clearly understood, so long as the application to turfgrass is concerned, it is considered that the silicone surfactant will impart a proper surface tension and spreading property to the treating liquid thereby to facilitate falling off of an excess treating liquid from turfgrass, which effectively contributes to the effects of the present invention.

Now, some embodiments of the present invention will be exemplified. However, it should be understood that the present invention is by no means restricted thereto.

Embodiments of treatment with the herbicidal compound and the silicone surfactant will be exemplified below.

(1) A method wherein a herbicidal compound is diluted with water containing a silicone surfactant in a proportion of from 0.005 to 0.5 vol %, and applied to a site where turfgrass less sensitive to the herbicidal compound is planted, thereby to reduce undesirable effects on nearby turfgrass highly sensitive to the herbicidal compound.

(2) A method wherein a herbicidal compound and a silicone surfactant are applied to a site where turfgrass less sensitive to the herbicidal compound is planted, thereby to reduce undesirable effects on nearby turfgrass highly sensitive to the herbicidal compound, which will be caused via contact with the turfgrass or unwanted plants at the treated site.

(3) A method wherein a herbicidal compound and a silicone surfactant are applied to a site where turfgrass less sensitive to the herbicidal compound is planted, thereby to reduce undesirable effects on nearby turfgrass highly sensitive to the herbicidal compound, which will be caused via indirect contact with the turfgrass or unwanted plants at the treated site.

(4) A method wherein a herbicidal compound and a silicone surfactant are applied to a site where turfgrass less susceptible to the herbicidal compound is planted, thereby to reduce undesirable effects to nearby turfgrass highly sensitive to the herbicidal compound, which will be caused via soles of shoes, a chemical treatment tool, a watering tool or a lawn-mowing tool, which was in contact with turfgrass or unwanted plants at the treated site.

(5) A method wherein a herbicidal compound and a silicone surfactant are applied to a site where turfgrass less sensitive to the herbicidal compound is planted, thereby to reduce undesired effects on nearby turfgrass highly sensitive to the herbicidal compound, which will be caused via soles of shoes; hoses or wheels of a chemical treatment tool; hoses or wheels of a watering tool; or a lawn-mowing tool or its wheels, which were in contact with the turfgrass or unwanted plants at the treated site.

The present invention is useful to reduce undesirable effects on nearby turfgrass highly sensitive to the herbicidal compound, which will be caused after application of the herbicidal compound.

Further, a case where undesirable effects are caused by bringing in the above herbicidal compound from the site where the herbicidal compound was applied, to nearby turfgrass highly sensitive to the herbicidal compound, is also included in the present invention.

In the present invention, "bringing in" means transferring the herbicidal compound from a site to another site i.e. from a site to which the herbicidal compound was applied to nearby turfgrass highly sensitive to the herbicidal compound, via direct or indirect contact.

The present invention is particularly useful in a golf course where turfgrass less sensitive to a herbicidal compound and turfgrass highly sensitive thereto are planted. An embodiment of such a case is exemplified below.

(6) A method wherein in a golf course where less sensitive turfgrass and highly sensitive turfgrass are planted, a herbicidal compound and a silicone surfactant are applied to a site where turfgrass less sensitive to the herbicidal compound is planted, thereby to reduce undesirable effects on turfgrass highly sensitive to the herbicidal compound.

EXAMPLES

The present invention will be described in further detail with reference to Examples, but it should be understood that the present invention is by no means limited thereto.

Example 1

Soil was put into a 1/300,000 ha pot, and mascarenegrass was cultivated. Further, soil was put into a 1/1,000,000 ha pot, and bentgrass (breed: penncross) was cultivated. A predetermined amount (flazasulfuron: 50 g a.i./ha) of water dispersible granules (tradename: SHIBAGEN DF, manufactured by Ishihara Sangyo Kaisha, Ltd.) containing flazasulfuron as an active ingredient, was diluted with water containing a predetermined amount of a silicone surfactant (tradename: Maku-pika, manufactured by Ishihara Sangyo Kaisha, Ltd.) and applied by foliar treatment to the mascarenegrass by a small spraygun so that the amount of the treating liquid corresponds to 2,000 L/ha. Immediately after the treatment or upon expiration of 6 hours after the treatment, the bentgrass not treated with flazasulfuron was rubbed against the mascarenegrass treated with flazasulfuron (the pot of bentgrass was permitted to slide and reciprocate once).

On 14th day after the treatment with flazasulfuron, the state of growth of the bentgrass was visually observed and investigated, and the growth inhibition rate and the degree of necrosis evaluated in accordance with the following standards are shown in Tables 1 and 2. Further, as comparative areas, an area wherein polyoxyethylene octylphenyl ether (tradename: Kusa-rino, manufactured by Nihon nohyaku Co., Ltd.) was used as a surfactant commonly employed in this field, and an area wherein no surfactant was used, were provided.

Growth inhibition rate (%)=0 (equivalent to non-treated area) to 100 (complete kill)
Degree of necrosis=0 (equivalent to non-treated area) to 5.0 (maximum)

TABLE 1

(Rubbed immediately after treatment with flazasulfuron)

| | Surfactant | | Bentgrass | |
| --- | --- | --- | --- | --- |
| | Tradename | Concentration (vol %) | Growth inhibition rate (%) | Necrosis |
| Present invention area | Maku-pika | 0.02 | 53 | 1.3 |
| | | 0.033 | 35 | 0.5 |
| Comparative area | Kusa-rino | 0.02 | 67 | 2.0 |
| | Not added | — | 48 | 0.8 |

TABLE 2

(Rubbed upon expiration of 6 hours after treatment with flazasulfuron)

| | Surfactant | | Bentgrass | |
| --- | --- | --- | --- | --- |
| | Tradename | Concentration (vol %) | Growth inhibition rate (%) | Necrosis |
| Present invention area | Maku-pika | 0.02 | 0 | 0 |
| Comparative area | Kusa-rino | 0.02 | 30 | 0 |

Example 2

Japanese lawngrass was cultivated on ground in 0.6 m$^2$ (0.4 m×1.5 m). Further, soil was put into a 1/300,000 ha pot, and bentgrass (breed: penncross) was cultivated. A predetermined amount (flazasulfuron: 50 g a.i./ha) of SHIBAGEN DF (tradename, the same as in Example 1) was diluted with water containing a predetermined amount of Maku-pika (tradename, the same as in Example 1) and applied by foliar treatment to the Japanese lawngrass by a small spraygun so that the amount of the treating liquid corresponds to 2,000 L/ha. Immediately after the treatment or upon expiration of 3 hours after the treatment, a tester walked (5 steps) on the Japanese lawngrass treated with flazasulfuron and then stepped on the bentgrass.

On 21st day after treatment with flazasulfuron, the state of growth of the bentgrass was evaluated in the same manner as in Example 1, and the growth inhibition rate is shown in Tables 3 and 4. Further, as comparative areas, an area wherein Kusa-rino (tradename, the same as in Example 1) was used, and an area wherein no surfactant was used, were provided.

TABLE 3

(Stepped on immediately after treatment with flazasulfuron)

| | Surfactant | | Bentgrass |
| --- | --- | --- | --- |
| | Tradename | Concentration (vol %) | Growth inhibition rate (%) |
| Present invention area | Maku-pika | 0.02 | 25 |
| Comparative area | Kusa-rino | 0.02 | 35 |
| | Not added | — | 30 |

TABLE 4

(Stepped on upon expiration of 3 hours
after treatment with flazasulfuron)

| | Surfactant | | Bentgrass |
|---|---|---|---|
| | Tradename | Concentration (vol %) | Growth inhibition rate (%) |
| Present invention area | Maku-pika | 0.02 | 15 |
| Comparative area | Kusa-rino | 0.02 | 23 |

Example 3

On ground, Japanese lawngrass in 50 m² (2 m×25 m) and bentgrass (breed: penncross) in 0.12 m² (0.35 m×0.35 m) were respectively cultivated. A predetermined amount (flazasulfuron: 50 g a.i./ha) of SHIBAGEN DF (tradename, the same as in Example 1) was diluted with water containing a predetermined amount of Maku-pika (tradename, the same as in Example 1) and applied by foliar treatment to the Japanese lawngrass by a knapsack power sprayer so that the amount of the treating liquid corresponds to 2,000 L/ha. Immediately after the treatment or next day after the treatment, a tester walked (50 m) on the Japanese lawngrass treated with flazasulfuron, then walked (10 m) on Japanese lawngrass not treated with a treating agent and then stepped on the bentgrass.

On 22nd day after the treatment with flazasulfuron, the state of growth of the bentgrass was visually observed and investigated, and the growth inhibition rate and the degree of discoloring evaluated in accordance with the following standards are shown in Tables 5 and 6. Further, as a comparative area, an area wherein Kusa-rino (tradename, the same as in Example 1) was used, was provided.

Growth inhibition rate (%)=0 (equivalent to non-treated area) to 100 (complete kill)

Degree of discoloring=0 (equivalent to non-treated area) to 5.0 (maximum)

TABLE 5

(Stepped on immediately after treatment with flazasulfuron)

| | Surfactant | | Bentgrass | |
|---|---|---|---|---|
| | Tradename | Concentration (vol %) | Growth inhibition rate (%) | Discoloring |
| Present invention area | Maku-pika | 0.03 | 25 | 1.5 |
| Comparative area | Kusa-rino | 0.02 | 28 | 2.3 |

TABLE 6

(Stepped on next day after treatment with flazasulfuron)

| | Surfactant | | Bentgrass | |
|---|---|---|---|---|
| | Tradename | Concentration (vol %) | Growth inhibition rate (%) | Discoloring |
| Present invention area | Maku-pika | 0.03 | 28 | 1.8 |

TABLE 6-continued (Stepped on next day after treatment with flazasulfuron)

| | Surfactant | | Bentgrass | |
|---|---|---|---|---|
| | Tradename | Concentration (vol %) | Growth inhibition rate (%) | Discoloring |
| Comparative area | Kusa-rino | 0.02 | 35 | 2.5 |

Example 4

On ground, mascarenegrass in 50 m² (2 m×25 m) and bentgrass (breed: Minakuru) in 0.12 m² (0.35 m×0.35 m) were respectively cultivated. A predetermined amount (flazasulfuron: 100 g a.i./ha) of a wettable powder containing flazasulfuron as an active ingredient (tradename: SHIBAGEN WP, manufactured by Ishihara Sangyo Kaisha, Ltd.) was diluted with water containing a predetermined amount of a silicone surfactant (tradename: Silwet L-77, manufactured by Witco) and applied by foliar treatment to the mascarenegrass by a knapsack power sprayer so that the amount of the treating liquid corresponds to 2,000 L/ha. After the treating liquid dried, a tester walked (100 m) on the mascarenegrass treated with flazasulfuron, then walked (10 m) on mascarenegrass not treated with flazasulfuron and then stepped on five times on the bentgrass.

On 11th day after the treatment with flazasulfuron, the state of growth of the bentgrass was evaluated in the same manner as in Example 3, and the growth inhibition rate and the degree of discoloring are shown in Table 7. Further, as comparative areas, an area wherein Kusa-rino (tradename, the same as in Example 1) was used, and an area wherein no surfactant was used, were provided.

TABLE 7

| | Surfactant | | Bentgrass | |
|---|---|---|---|---|
| | Tradename | Concentration (vol %) | Growth inhibition rate (%) | Discoloring |
| Present invention area | Silwet L-77 | 0.1% | 20 | 0.5 |
| Comparative area | Kusa-rino | 0.05% | 35 | 1.0 |
| | Not added | — | 28 | 1.0 |

Example 5

Soil was put into a 1/300,000 ha pot, and mascarenegrass was cultivated. Further, soil was put into a 1/1,000,000 ha pot, and bentgrass (breed: penncross) was cultivated. A predetermined amount (trifloxysulfuron sodium salt: 45 g a.i./ha) of water dispersible granules containing trifloxysulfuron sodium salt as an active ingredient (tradename: Monument water dispersible granules, manufactured by Syngenta Japan K.K.) was diluted with water containing a predetermined amount of Maku-pika (tradename, the same as in Example 1) and applied by foliar treatment to the mascarenegrass by a small spraygun, so that the amount of the treating liquid corresponds to 2,000 L/ha. Upon expiration of 6 hours after the treatment, the bentgrass not treated with trifloxysulfuron sodium salt, was rubbed against the mascarenegrass treated therewith (the pot of bentgrass was permitted to slide and reciprocate once).

On 12th day after the treatment with trifloxysulfuron sodium salt, the state of growth of the bentgrass was evaluated in the same manner as in Example 3, and the growth inhibition rate and the degree of discoloring are shown in Table 8. Further, as comparative areas, an area wherein Kusa-rino (tradename, the same as in Example 1) was used, and an area wherein no surfactant was used, were provided.

TABLE 8

(Rubbed upon expiration of 6 hours after treatment with trifloxysulfuron sodium salt)

| | Spreading agent | | Bentgrass Growth | |
|---|---|---|---|---|
| | Tradename | Concentration (wt %) | inhibition rate | Bentgrass Discoloring |
| Present invention area | Maku-pika | 0.1 | 39 | 0.5 |
| Comparative area | Kusa-rino | 0.02 | 50 | 1.0 |
| | Not added | — | 60 | 1.5 |

Example 6

Soil was put into a 1/300,000 ha pot, and mascarenegrass were cultivated. Further, soil was put into a 1/1,000,000 ha pot, and bentgrass (breed: penncross) was cultivated. A predetermined amount (asulam: 4625 g a.i./ha) of a treating liquid containing asulam as an active component (tradename: Arsilan liquid preparation, manufactured by Ishihara Sangyo Kaisha, Ltd.) was diluted with water containing a predetermined amount of Maku-pika (tradename, the same as in Example 1), and applied by foliar treatment to the mascarenegrass by a small spraygun so that the amount of the treating liquid corresponds to 2,000 L/ha. Upon expiration of 6 hours after the treatment, the bentgrass not treated with asulam was rubbed against the mascarenegrass treated therewith (the pot of bentgrass was permitted to slide and reciprocate once).

On 12th day after the treatment with asulam, the state of growth of the bentgrass was evaluated in the same manner as in Example 3, and the growth inhibition rate and the degree of discoloring are shown in Table 9. Further, as comparative areas, an area wherein Kusa-rino (tradename, the same as in Example 1) was used, and an area wherein no surfactant was used, were provided.

TABLE 9

(Rubbed upon expiration of 6 hours after treatment with asulam)

| | Spreading agent | | Bentgrass Growth | |
|---|---|---|---|---|
| | Tradename | Concentration (wt %) | inhibition rate | Bentgrass Discoloring |
| Present invention area | Maku-pika | 0.03 | 23 | 1.3 |
| | | 0.1 | 3 | 0 |
| Comparative area | Kusa-rino | 0.02 | 38 | 2.3 |
| | Not added | — | 45 | 2.5 |

Example 7

Soil was put into a 1/300,000 ha pot, and mascarenegrass was cultivated. Further, soil was put into a 1/1,000,000 ha pot, and bentgrass (breed: penncross) was cultivated. A predetermined amount (rimsulfuron: 35.25 g a.i./ha) of water dispersible granules containing rimsulfuron as an active ingredient (tradename: Hurley DF, manufactured by MARUWA Biochemical Co., Ltd.) was diluted with water containing a predetermined amount of Maku-pika (tradename, the same as in Example 1) and applied by foliar treatment to the mascarenegrass by a small spraygun, so that the amount of the treating liquid corresponds to 2,000 L/ha. Upon expiration of 6 hours after the treatment, the bentgrass not treated with rimsulfuron was rubbed against the mascarenegrass treated therewith (the pot of bentgrass was permitted to slide and reciprocate once).

On 13th day after the treatment with rimsulfuron, the state of growth of the bentgrass was evaluated in the same manner as in Example 3, and the growth inhibition rate and the degree of discoloring are shown in Table 10. Further, as comparative areas, an area wherein Kusa-rino (tradename, the same as in Example 1) or Surfactant WK (tradename, manufactured by MARUWA Biochemical Co., Ltd.) was used, and an area wherein no surfactant was used, were provided.

TABLE 10

(Rubbed upon expiration of 6 hours after treatment with rimsulfuron)

| | Spreading agent | | Bentgrass Growth | |
|---|---|---|---|---|
| | Tradename | Concentration (wt %) | inhibition rate | Bentgrass Discoloring |
| Present invention area | Maku-pika | 0.03 | 23 | 0.5 |
| Comparative area | Surfactant WK | 0.03 | 33 | 0.8 |
| | Kusa-rino | 0.03 | 48 | 1.5 |
| | Not added | — | 35 | 1.0 |

Example 8

Soil was put into a 1/300,000 ha pot, and mascarenegrass was cultivated. Further, soil was put into a 1/1,000,000 ha pot, and bentgrass (breed: penncross) was cultivated. A predetermined amount (nicosulfuron: 40 g a.i./ha) of an emulsifiable concentrate containing nicosulfuron as an active ingredient (tradename: Onehope emulsifiable concentrate, manufactured by Ishihara Sangyo Kaisha, Ltd.) was diluted with water containing a predetermined amount of Maku-pika (tradename, the same as in Example 1) and applied by foliar treatment to the mascarenegrass by a small spraygun, so that the amount of the treating liquid corresponds to 2,000 L/ha. Immediately after the treatment, the bentgrass not treated with nicosulfuron, was rubbed against the mascarenegrass treated therewith (the pot of bentgrass was permitted to slide and reciprocate once).

On 28th day after the treatment with nicosulfuron, the state of growth of the bentgrass was evaluated in the same manner as in Example 3, and the growth inhibition rate and the degree of discoloring are shown in Table 11. Further, as a comparative area, an area wherein Surfactant WK (tradename, the same as in Example 7) was used, was provided.

TABLE 11

(Rubbed immediately after treatment with nicosulfuron)

| | Spreading agent | | Bentgrass Growth | |
|---|---|---|---|---|
| | Tradename | Concentration (wt %) | inhibition rate | Bentgrass Discoloring |
| Present invention area | Maku-pika | 0.05 | 60 | 1.9 |
| Comparative area | Surfactant WK | 0.05 | 65 | 2.3 |

Example 9

Soil was put into a 1/300,000 ha pot, and mascarenegrass was cultivated. Further, soil was put into a 1/1,000,000 ha pot, and bentgrass (breed: penncross) was cultivated. A predetermined amount (florasulam: 36 g a.i./ha) of a liquid preparation containing florasulam as an active ingredient (tradename: Plimus, manufactured by Dow AgroSciences) was diluted with water containing a predetermined amount of Maku-pika (tradename, the same as in Example 1) and applied by foliar treatment to the mascarenegrass by a small spraygun, so that the amount of the treating liquid corresponds to 2,000 L/ha. Immediately after the treatment, the bentgrass not treated with florasulam was rubbed against the mascarenegrass treated therewith (the pot of bentgrass was permitted to slide and reciprocate once).

On 7th day after the treatment with florasulam, the state of growth of the bentgrass was evaluated in the same manner as in Example 3, and the growth inhibition rate and the degree of discoloring are shown in Table 12. Further, as a comparative area, an area wherein Surfactant WK (tradename, the same as in Example 7) was used, was provided.

TABLE 12

(Rubbed immediately after treatment with florasulam)

| | Spreading agent | | Bentgrass Growth | |
|---|---|---|---|---|
| | Tradename | Concentration (wt %) | inhibition rate | Bentgrass Discoloring |
| Present invention area | Maku-pika | 0.05 | 23 | 1.5 |
| Comparative area | Surfactant WK | 0.05 | 25 | 1.7 |

Example 10

Soil was put into a 1/300,000 ha pot, and mascarenegrass was cultivated. Further, soil was put into a 1/1,000,000 ha pot, and bentgrass (breed: penncross) was cultivated. A predetermined amount (flazasulfuron: 50 g a.i./ha) of SHIBAGEN DF (tradename, the same as in Example 1) was diluted with water containing a predetermined amount of a silicone surfactant (tradename: Breakthru, manufactured by Sankei Chemical Co., Ltd.) and applied by foliar treatment to the mascarenegrass by a small spraygun, so that the amount of the treating liquid corresponds to 2,000 L/ha. Upon expiration of 6 hours after the treatment, the bentgrass not treated with flazasulfuron, was rubbed against the mascarenegrass treated therewith (the pot of bentgrass was permitted to slide and reciprocate once).

On 21st day after the treatment with flazasulfuron, the state of growth of the bentgrass was evaluated in the same manner as in Example 3, and the growth inhibition rate and the degree of discoloring are shown in Table 13. Further, as comparative areas, an area wherein Kusa-rino (tradename, the same as in Example 1) was used, and an area wherein no surfactant was used, were provided.

TABLE 13

(Rubbed upon expiration of 6 hours after treatment with flazasulfuron)

| | Spreading agent | | Bentgrass Growth | |
|---|---|---|---|---|
| | Tradename | Concentration (wt %) | inhibition rate | Bentgrass Discoloring |
| Present invention area | Breakthru | 0.03 | 34 | 0 |
| Comparative area | Kusa-rino | 0.02 | 57 | 0.3 |
| | Not added | — | 57 | 0.5 |

INDUSTRIAL APPLICABILITY

According to the present invention, at a site where turfgrass less sensitive to a herbicide to be used and turfgrass highly sensitive thereto are planted in the vicinity of each other, it is possible to manage the lawn without bringing about undesirable effects on the highly sensitive turfgrass.

The entire disclosure of Japanese Patent Application No. 2010-046200 filed on Mar. 3, 2010 including specification, claims and abstract is incorporated herein by reference in its entirety.

The invention claimed is:

1. A method of treating turfgrass, comprising applying a treatment liquid comprising water, a herbicidal compound and 0.005 to 0.5 vol % of a silicone surfactant to a first turfgrass which is in direct or indirect contact with a second turfgrass, wherein the first turfgrass is less sensitive to the herbicidal compound as compared to the second turfgrass, wherein the silicone surfactant is a compound represented by the following formula (I):

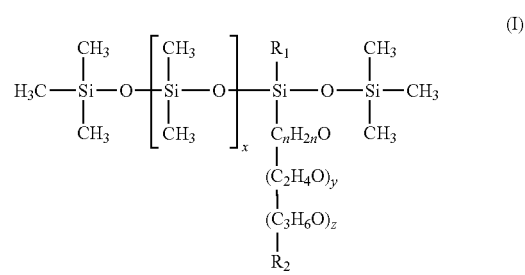

wherein $R_1$ is a hydrogen atom or a methyl group, $R_2$ is a hydrogen atom, a hydroxy group, a methyl group or an acetyl group, n is an integer of from 0 to 4, x is an integer of from 0 to 2, y is an integer of from 1 to 15, and z is an integer of from 0 to 10, to reduce one or more undesirable effects selected from the group consisting of discoloring, brown discoloration, necrosis, chlorosis, anthocyan and growth inhibition on the second turfgrass caused by the herbicidal compound.

2. The method according to claim 1, wherein the herbicidal compound is at least one member selected from the group consisting of acetolactate synthase (ALS) inhibitors and mitotic inhibitors.

3. The method according to claim 2, wherein the herbicidal compound is an acetolactate synthase (ALS) inhibitor.

4. The method according to claim 3, wherein the acetolactate synthase (ALS) inhibitor is at least one compound or its salt selected from the group consisting of a sulfonylurea compound, a pyrimidine compound and a triazolopyrimidine compound.

5. The method according to claim 4, wherein the sulfonylurea compound is at least one compound selected from the group consisting of flazasulfuron, cinosulfuron, rimsulfuron, trifloxysulfuron, chlorimuron ethyl, iodosulfuron methyl, foramsulfuron, nicosulfuron, sulfosulfuron and chlorosulfuron, the pyrimidine compound is pyrimisulfan, and the triazolopyrimidine compound is florasulam.

6. The method according to claim 4, wherein the sulfonylurea compound is at least one compound selected from the group consisting of flazasulfuron, rimsulfuron, trifloxysulfuron and nicosulfuron, and the triazolopyrimidine compound is florasulam.

7. The method according to claim 2, wherein the herbicidal compound is a mitotic inhibitor.

8. The method according to claim 7, wherein the mitotic inhibitor is a carbamate compound.

9. The method according to claim 8, wherein the carbamate compound is asulam.

10. The method according to claim 1, wherein the herbicidal compound is flazasulfuron and the silicone surfactant is polyoxyethylene methyl-polysiloxane.

11. The method according to any one of claims 1 to 10, wherein the undesirable effects are caused via contact with turfgrass or at the site to which the herbicidal compound and the silicone surfactant are applied.

12. The method according to any one of claims 1 to 10, wherein the undesirable effects are caused via a shoe sole, a chemical treatment tool, a watering tool or a lawn-mowing tool contacted with turfgrass or at the site to which the herbicidal compound and the silicone surfactant are applied.

* * * * *